(12) United States Patent
Faraj

(10) Patent No.: US 9,271,990 B2
(45) Date of Patent: Mar. 1, 2016

(54) FULVESTRANT FORMULATIONS

(71) Applicant: Fresenius Kabi USA, LLC, Lake Zurich, IL (US)

(72) Inventor: Jabar A. Faraj, Skokie, IL (US)

(73) Assignee: Fresenius Kabi USA, LLC, Lake Zurich, IL (US)

( * ) Notice: Subject to any disclaimer, the term of this patent is extended or adjusted under 35 U.S.C. 154(b) by 92 days.

(21) Appl. No.: 14/181,244

(22) Filed: Feb. 14, 2014

(65) Prior Publication Data

US 2015/0231153 A1      Aug. 20, 2015

(51) Int. Cl.
*A61K 31/565* (2006.01)

(52) U.S. Cl.
CPC .................................. *A61K 31/565* (2013.01)

(58) Field of Classification Search
None
See application file for complete search history.

(56) References Cited

U.S. PATENT DOCUMENTS

| | | | |
|---|---|---|---|
| 5,183,814 A | 2/1993 | Dukes | |
| 6,774,122 B2 | 8/2004 | Evans et al. | |
| 7,456,160 B2 | 11/2008 | Evans et al. | |
| 8,247,423 B2 | 8/2012 | Estok et al. | |
| 8,329,680 B2 | 12/2012 | Evans et al. | |
| 8,466,139 B2 | 6/2013 | Evans et al. | |
| 2003/0125387 A1 | 7/2003 | Evans et al. | |
| 2004/0175402 A1 | 9/2004 | Gellert et al. | |
| 2007/0053869 A1 | 3/2007 | Sugiyama et al. | |
| 2009/0227549 A1 | 9/2009 | Palepu | |
| 2010/0015184 A1 | 1/2010 | Tuel | |
| 2010/0021416 A1 | 1/2010 | Lichter et al. | |
| 2010/0239667 A1 | 9/2010 | Hemmingsen et al. | |
| 2010/0266590 A1 | 10/2010 | Demetri et al. | |
| 2010/0278784 A1 | 11/2010 | Pojasek et al. | |
| 2011/0230569 A1 | 9/2011 | Nistor et al. | |
| 2011/0318420 A1 * | 12/2011 | Hu et al. ....................... 424/489 |
| 2012/0329766 A1 | 12/2012 | Evans et al. | |
| 2013/0029948 A1 | 1/2013 | Roppe et al. | |
| 2013/0267489 A1 | 10/2013 | Teja et al. | |

FOREIGN PATENT DOCUMENTS

| | | |
|---|---|---|
| EP | 1854463 A1 | 11/2007 |
| WO | WO 03/006064 A1 | 1/2003 |

OTHER PUBLICATIONS

Unknown, "Patent Issued for Formulation," *Biotech Week*: p. 1154 (Dec. 26, 2012).
AstraZeneca, "Prescribing Information for FASLODEX™ (Fulvestrant) Injection" (Nov. 2012).

* cited by examiner

*Primary Examiner* — Theodore R West
(74) *Attorney, Agent, or Firm* — Leydig, Voit & Mayer, Ltd.

(57) ABSTRACT

The invention provides a fulvestrant composition comprising a pharmaceutically acceptable alcohol, polysorbate 80, an antioxidant, and castor oil, which is substantially or completely free of a non-aqueous ester solvent and which demonstrates excellent storage stability. The composition may be used to treat hormone receptor positive metastatic breast cancer in a subject.

17 Claims, 1 Drawing Sheet

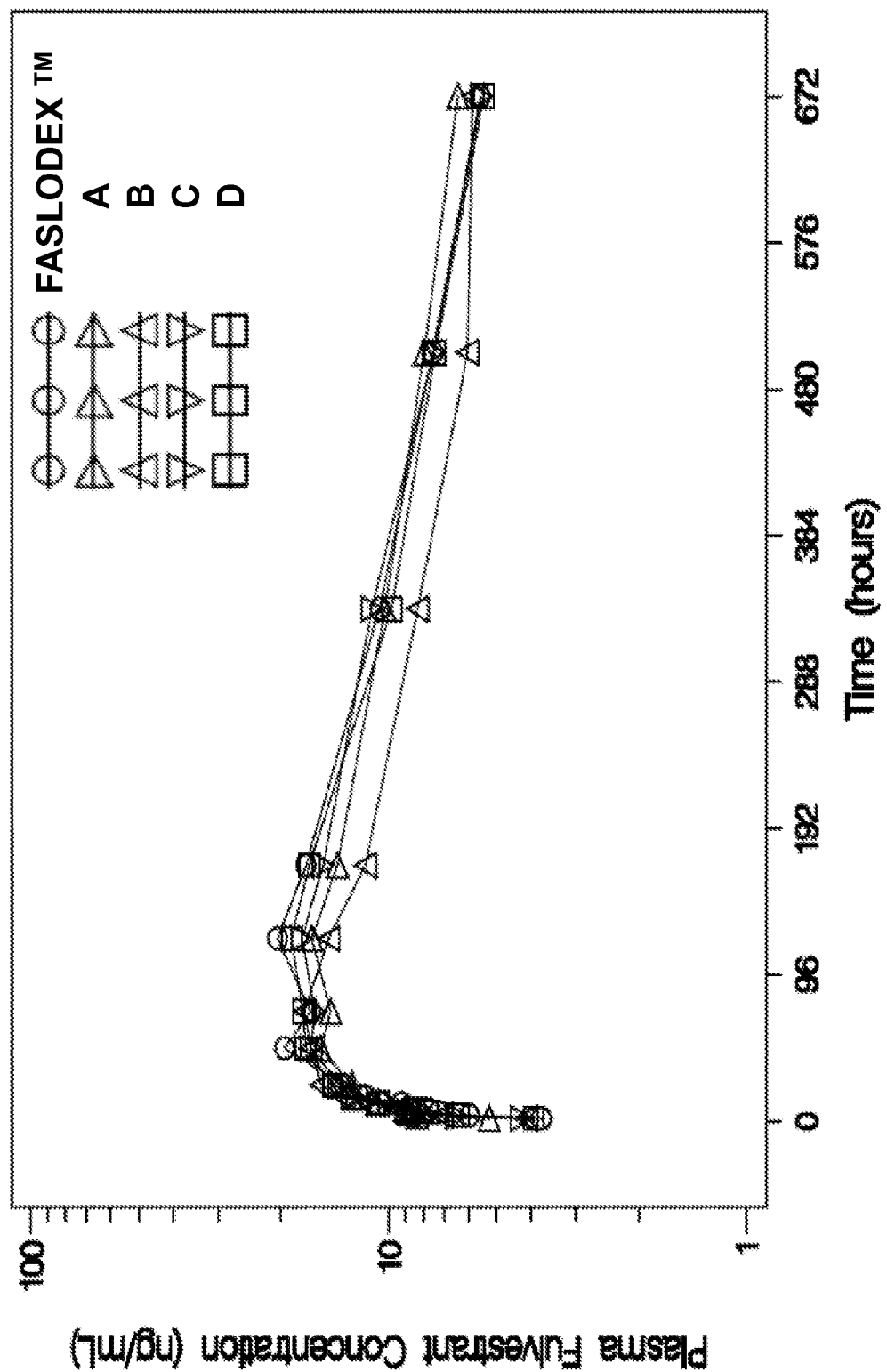

FULVESTRANT FORMULATIONS

BACKGROUND OF THE INVENTION

Fulvestrant is an estrogen receptor antagonist, which was approved in the United States in 2002 under the tradename FASLODEX™ for the treatment of hormone receptor positive metastatic breast cancer in postmenopausal women with disease progression following antiestrogen therapy. The FASLODEX™ (fulvestrant) product is approved for administration by intramuscular injection on days 1, 15, 29, and once monthly thereafter. Current guidelines recommend that a volume of no more than 5 mL is administered in a single intramuscular injection. However, fulvestrant is a highly lipophilic molecule which is practically insoluble in water. Therefore, a formulation which contains enough fulvestrant to provide therapeutic efficacy over a period of several days or weeks in a volume of 5 mL or less is desirable.

U.S. Pat. Nos. 6,774,122; 7,456,160; 8,329,680; and 8,466,139 disclose that the introduction of a non-aqueous ester solvent which is miscible in castor oil and an alcohol surprisingly eases the solubilization of fulvestrant into a concentration of at least 50 mg/mL. These patents disclose benzyl benzoate, ethyl oleate, isopropyl myristate, and isopropyl palmitate as preferred non-aqueous ester solvents, most preferably benzyl benzoate at a concentration of 15% w/v. The formulations disclosed in U.S. Pat. Nos. 6,774,122; 7,456,160; 8,329,680; and 8,466,139 encompass the FASLODEX™ (fulvestrant) product, which comprises 250 mg fulvestrant in a 5 mL solution containing 10% w/v alcohol, 10% w/v benzyl alcohol, and 15% w/v benzyl benzoate as cosolvents which is made up to 100% w/v with castor oil as a cosolvent and a release rate modifier (FASLODEX™ Prescribing Information, Rev. 11/12). The Prescribing Information for FASLODEX™ (fulvestrant) injection indicates that the product should be stored under refrigeration at 2°-8° C. until time of use.

Other formulations of fulvestrant have been described. U.S. Pat. No. 5,183,814 discloses a formulation comprising 50 mg fulvestrant and 400 mg benzyl alcohol, which is made up to 1 mL with castor oil. U.S. Patent Application Publication 2004/0175402 discloses a formulation adapted for administration by injection containing fulvestrant in a ricinoleate vehicle comprising an antioxidant, such as thiourea, to suppress the formation of fulvestrant oxidative degradation products and improve formulation stability. International Patent Application Publication WO 2003/006064 discloses a formulation containing fulvestrant in a ricinoleate vehicle comprising at least one alcohol and a non-aqueous ester solvent, wherein the concentration of fulvestrant is at least 100 mg/mL to facilitate less frequent dosing intervals or the administration of a higher drug dose.

U.S. Patent Application Publication 2009/0227549 discloses a formulation suitable for intramuscular administration comprising at least 40 mg/mL fulvestrant in a vehicle, wherein the formulation is substantially free of castor oil and castor oil derivatives. U.S. Patent Application Publication 2013/0267489 discloses a composition comprising fulvestrant; a solvent selected from dimethyl sulfoxide (DMSO), glycofurol, N-methyl pyrrolidone, and mixtures thereof; an oil mixture selected from a mixture of caprylic and capric triglycerides, a mixture of caprylic, capric and linoleic triglycerides, a mixture of caprylic, capric and succinic triglycerides, and a mixture of propylene glycol dicaprylate and propylene glycol dicaprate; and a sustained release member selected from benzyl benzoate, dihydrolipoic acid, benzyl alcohol and lipoic acid, which has less than about 5% total impurities after at least about 24 months of storage at about 5°-25° C.

There remains a need for formulations comprising a therapeutically effective amount of fulvestrant in a pharmaceutically acceptable vehicle suitable for intramuscular injection which are storage stable, preferably for long durations at room temperature.

BRIEF SUMMARY OF THE INVENTION

An embodiment of the invention provides a composition which contains fulvestrant, a pharmaceutically acceptable alcohol, polysorbate 80, an antioxidant, and castor oil.

Another embodiment of the invention provides a method of stabilizing a fulvestrant composition, by forming a mixture comprising fulvestrant, a pharmaceutically acceptable alcohol, polysorbate 80, an antioxidant, and castor oil.

In yet another embodiment, the composition of the invention is formulated for parenteral administration and may be presented in a container selected from the group consisting of a vial, a bottle, a cartridge, and a syringe.

The composition according to the invention is storage stable and suitable for administration to a subject to treat or prevent a disease or condition, such as breast cancer.

Other embodiments, characteristics, and advantages of the invention will be more apparent after reading the description and the examples that follow.

BRIEF DESCRIPTION OF THE SEVERAL VIEWS OF THE DRAWING(S)

FIG. 1 depicts the time course of fulvestrant plasma concentration upon administration to rabbits of a reference castor oil-based formulation representing the FASLODEX™ (fulvestrant) injection product ("RLD"), or one of four castor oil-based formulations according to the invention comprising 10% w/v benzyl alcohol, 0.12% w/v polysorbate 80, 0.06% w/v α-tocopherol, 10% w/v ethanol, and 7.5% w/v fulvestrant ("A"), 10% w/v benzyl alcohol, 0.12% w/v polysorbate 80, 0.06% w/v α-tocopherol, 15% w/v ethanol, and 10% w/v fulvestrant ("B"), 10% w/v benzyl alcohol, 0.12% w/v polysorbate 80, 0.06% w/v α-tocopherol, 10% w/v ethanol, and 5% w/v fulvestrant ("C"), or 10% w/v benzyl alcohol, 0.12% w/v polysorbate 80, 0.06% w/v α-tocopherol, 17% w/v ethanol, and 5% w/v fulvestrant ("D"). Each data point represents the mean plasma fulvestrant concentration (n=6 rabbits per group).

DETAILED DESCRIPTION OF THE INVENTION

The invention provides a composition which contains fulvestrant, a pharmaceutically acceptable alcohol, polysorbate 80, an antioxidant, and castor oil.

Fulvestrant (7α-[9-(4,4,5,5,5-pentafluoropentylsulfinyl)nonyl]oestra-1,3,5(10)-triene 3,17 β-diol) has the following structural formula (1):

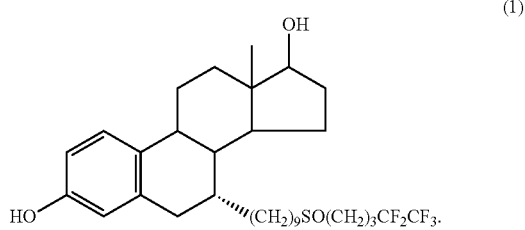

Fulvestrant contains six asymmetric carbon atoms and a stereogenic sulfoxide in the side chain. The active ingredient in the FASLODEX™ (fulvestrant) injection product is a mixture of 2 diastereoisomers, which are referred to in the art as fulvestrant sulfoxide A and B. Fulvestrant sulfoxide A and B have the same absolute configuration at each of the stereogenic centers in the steroid system, but different absolute configurations at the sulfur atom.

In any of the embodiments of the invention, the fulvestrant can be fulvestrant sulfoxide A, fulvestrant sulfoxide B, or a mixture of fulvestrant sulfoxide A and fulvestrant sulfoxide B. In addition, the fulvestrant can be in free form, or the fulvestrant can be in salt or solvate form, such as a pharmaceutically acceptable fulvestrant salt or fulvestrant solvate. Thus, all salt and non-salt forms of fulvestrant and solvates of the foregoing are embraced by the invention and descriptions of fulvestrant provided herein. The fulvestrant can be crystalline or amorphous. If crystalline, the fulvestrant can be any polymorphic form.

In some embodiments, the amount of fulvestrant present in the composition is 3% w/v (weight per volume of the composition) or more, e.g., 4% w/v or more, 5% w/v or more, 5.5% w/v or more, 6% w/v or more, 6.5% w/v or more, 7% w/v or more, 7.5% w/v or more, or 8% w/v or more. In other embodiments, the amount of fulvestrant present in the composition is 10% w/v or less, e.g., 9.5% w/v or less, 9% w/v or less, 8.5% w/v or less, 8% w/v or less, 7.5% w/v or less, 7% w/v or less, 6% w/v or less, or 5.5% w/v or less. In yet other embodiments, the amount of fulvestrant present in a composition is in a range bounded by any of the foregoing values. For example, the amount of fulvestrant present in a composition can be 3%-10% w/v, 4%-9% w/v, 4.5%-7.5% w/v, 5%-7.5% w/v, 5%-10% w/v, 6%-8% w/v, 7.5%-9.5% w/v, or 7%-10% w/v. In certain embodiments, the amount of fulvestrant present in a composition is about 5% w/v, or 50 mg/mL.

The pharmaceutically acceptable alcohol can be one alcohol or a mixture of two or more alcohols. In certain embodiments, the pharmaceutically acceptable alcohol is a mixture of two alcohols. Suitable pharmaceutically acceptable alcohols include, without limitation, ethanol, benzyl alcohol, or a mixture of both ethanol and benzyl alcohol.

In some embodiments, the amount of pharmaceutically acceptable alcohol present in the composition is 3% w/v or more, e.g., 5% w/v or more, 8% w/v or more, 10% w/v or more, 12.5% w/v or more, 15% w/v or more, 16.5% w/v or more, 17.5% w/v or more, or 19% w/v or more. In other embodiments, the amount of pharmaceutically acceptable alcohol present in the composition is 40% w/v or less, e.g., 35% w/v or less, 32.5% w/v or less, 27% w/v or less, 22.5% w/v or less, 21% w/v or less, 20% w/v or less, 18.5% w/v or less, or 17% w/v or less. In yet other embodiments, the amount of pharmaceutically acceptable alcohol present in a composition is in a range bounded by any of the foregoing values. For example, the amount of pharmaceutically acceptable alcohol present in a composition can be 3%-35% w/v, 8%-27% w/v, 10%-27% w/v, 15%-22.5% w/v, 17.5%-22.5% w/v, 19%-21% w/v, or 12.5%-17.5% w/v.

In certain embodiments, the composition comprises about 17% w/v ethanol and about 10% w/v benzyl alcohol. In some embodiments, the composition comprises a mixture of ethanol and benzyl alcohol present in approximately equivalent w/v amounts, for example, about 10% w/v ethanol and about 10% w/v benzyl alcohol.

It has been surprisingly found that the inclusion of polysorbate 80 in a castor oil-based composition facilitates the solubilization of fulvestrant into the composition at a concentration of 50 mg/mL or greater without the need for a non-aqueous ester solvent. Advantageously, upon administration to a subject, the composition of the invention provides pharmacokinetics which are similar to the pharmacokinetics provided by the FASLODEX™ (fulvestrant) injection product which contains, inter alia, 15% w/v benzyl benzoate.

Polysorbate 80 (polyoxyethylene (20) sorbitan monooleate) is a viscous, water soluble yellow liquid that functions in pharmaceutical formulations as a dispersing agent, an emollient, an emulsifying agent, a nonionic surfactant, a plasticizing agent, a solubilizing agent, a stabilizing agent, and/or a suspending agent. Polysorbate 80 is commercially available under the tradenames TWEEN™ 80, ALKEST™ TW 80, and CANARCEL™ TW 80.

In some embodiments, the amount of polysorbate 80 present in the composition is 0.005% w/v or more, e.g., 0.01% w/v or more, 0.05% w/v or more, 0.08% w/v or more, 0.10% w/v or more, 0.15% w/v or more, 0.2% w/v or more, 0.25% w/v or more, or 0.3% w/v or more. In other embodiments, the amount of polysorbate 80 present in the composition is 1.0% w/v or less, e.g., 0.75% w/v or less, 0.5% w/v or less, 0.25% w/v or less, 0.2% w/v or less, 0.16% w/v or less, 0.14% w/v or less, 0.09% w/v or less, or 0.07% w/v or less. In yet other embodiments, the amount of polysorbate 80 present in a composition is in a range bounded by any of the foregoing values. For example, the amount of polysorbate 80 present in a composition can be 0.005%-1.0% w/v, 0.01%-0.5% w/v, 0.05%-0.2% w/v, 0.08%-0.16% w/v, 0.10%-0.14% w/v, 0.15%-0.25% w/v, or 0.2%-0.5% w/v. In certain embodiments, the amount of polysorbate 80 present in a composition is about 0.12% w/v.

In certain embodiments of the invention, the antioxidant is a pharmaceutically acceptable antioxidant. The antioxidant can be one antioxidant or a mixture of two or more antioxidants. One of ordinary skill in the art will understand that the amount of antioxidant necessary to suppress the formation of oxidative degradation products in a composition of the invention will vary based upon the selected antioxidant and can be determined empirically through routine experimentation. Suitable antioxidants and general concentration ranges are described, for example, in "Remington: The Science and Practice of Pharmacy," $21^{st}$ edition, ed. P. Beringer, Lippincott Williams & Wilkins (2005) and in "Handbook of Pharmaceutical Excipients," $7^{th}$ edition, ed. R. Rowe, Pharmaceutical Press (2012).

In some embodiments, the antioxidant is a vitamin E compound, including one or more of $\alpha$-, $\beta$-, $\gamma$-, or $\delta$-tocopherol, and/or $\alpha$-, $\beta$-, $\gamma$-, or $\delta$-tocotrienol. The tocopherol or tocotrienol can be a d-tocopherol or d-tocotrienol (2R configuration), an l-tocopherol or l-tocotrienol (2S configuration), or a mixture of a d,l-tocopherol and/or d, l-tocotrienol.

In certain embodiments, the antioxidant is $\alpha$-tocopherol. In some embodiments, the amount of $\alpha$-tocopherol present in the composition is 0.001% w/v or more, e.g., 0.005% w/v or more, 0.01% w/v or more, 0.04% w/v or more, 0.08% w/v or more, 0.12% w/v or more, 0.18% w/v or more, 0.2% w/v or more, or 0.4% w/v or more. In other embodiments, the amount of $\alpha$-tocopherol present in the composition is 12% w/v or less, e.g., 8% w/v or less, 4% w/v or less, 2% w/v or less, 1% w/v or less, 0.8% w/v or less, 0.5% w/v or less, 0.1% w/v or less, or 0.08% w/v or less. In yet other embodiments, the amount of $\alpha$-tocopherol present in a composition is in a range bounded by any of the foregoing values. For example, the amount of $\alpha$-tocopherol present in a composition can be 0.005%-2.0% w/v, 0.01%-1% w/v, 0.01%-0.5% w/v, 0.04%-0.1% w/v, 0.04%-0.08% w/v, 0.12%-0.8% w/v, or 0.2%-0.5% w/v. In certain embodiments, the amount of $\alpha$-tocopherol present in a composition is about 0.06% w/v.

The vehicle for the composition which contains fulvestrant, a pharmaceutically acceptable alcohol, polysorbate 80, and an antioxidant in an oleaginous vehicle. Preferably, the oleaginous vehicle is a ricinoleate vehicle, such as castor oil. In certain embodiments, the castor oil is a super refined castor oil characterized by reduced carbonyl value, reduced peroxide value, reduced iodine value, and/or increased clarity as compared to USP grade castor oil. For example, in some embodiments, the castor oil used in a composition of the invention has a carbonyl value of 0.5 micromole/gram or less, a peroxide value of 5.0 meq $O_2$/kg or less, an iodine value of 85 g iodine/100 g castor oil or less, and/or a Gardner 1933 value of 1.5 or less.

Methods to determine carbonyl value, peroxide value, iodine value, and clarity of a sample of castor oil are known to those of skill in the art. For example, carbonyl values can be determined by incubating a sample of castor oil with excess 2,4-dinitrophenylhydrazine and a trichloroacetic acid catalyst in toluene for 30 minutes at 60° C., quenching with ethanolic KOH, and measuring absorbance of 2,4-dinitrophenylhydrazine derivatives at 430 nm and 460 nm by UV-VIS spectroscopy. Peroxide and iodine values can be determined using the current USP method 401 in conjunction with comparative titration. Clarity can be measured by comparing the color of a sample of castor oil to standards having known Gardner color numbers.

In some embodiments, the amount of castor oil present in the composition is 30% w/v or more, e.g., 40% w/v or more, 50% w/v or more, 60% w/v or more, 65% w/v or more, 70% w/v or more, 75% w/v or more, or 80% w/v or more. In other embodiments, the amount of castor oil present in the composition is 90% w/v or less, e.g., 85% w/v or less, 82% w/v or less, 77% w/v or less, 72% w/v or less, 67% w/v or less, 62% w/v or less, or 58% w/v or less. In yet other embodiments, the amount of castor oil present in a composition is in a range bounded by any of the foregoing values. For example, the amount of castor oil present in a composition can be 40%-85% w/v, 50%-77% w/v, 60%-82% w/v, 70%-85% w/v, 60%-77% w/v, 65%-72% w/v, or 75%-82% w/v.

In certain embodiments of the invention, the composition is substantially free of a non-aqueous ester solvent. As used herein, when referencing the amount of a component in a composition (or formulation, mixture, etc.) the term "substantially free" means not more than about 1.0%, e.g., not more than about 0.5%, not more than about 0.25%, not more than about 0.1%, not more than about 0.05%, not more than about 0.025%, or not more than about 0.01% of the component with reference to the complete composition as measured using standard analytical techniques.

In certain embodiments of the invention, the composition is completely free of a non-aqueous ester solvent, i.e., the composition contains no detectable amount of non-aqueous ester solvent as measured using standard analytical techniques.

The composition that includes fulvestrant, a pharmaceutically acceptable alcohol, polysorbate 80, an antioxidant, and castor oil may further include one or more other substances. Non-limiting examples of other substances include diluents, salts, buffers, stabilizers, solubilizers, preservatives, and tonicity modifiers.

A composition comprising fulvestrant, a pharmaceutically acceptable alcohol, polysorbate 80, an antioxidant, and castor oil can be prepared by any suitable method. In some embodiments, the composition is formed by combining the components together in a suitable vessel. The components can be combined in any order. In some embodiments, the pharmaceutically acceptable alcohol is added to a suitable vessel, the fulvestrant is added, and the mixture is stirred until the fulvestrant is dissolved. Subsequently, the polysorbate 80 and α-tocopherol are added to the vessel, and the mixture is stirred. Next, the castor oil is added to the vessel until the final volume is obtained, and the mixture is stirred. In other embodiments, the pharmaceutically acceptable alcohol, polysorbate 80, and α-tocopherol are combined in a suitable vessel prior to the addition of the fulvestrant. In certain embodiments, the vessel is pressurized with nitrogen upon the addition of the castor oil.

In some embodiments, the composition is filtered through one or more filters prior to filling the composition into one or more suitable containers, such as a vial, an ampoule, a cartridge, or a syringe. Preferably, one or more of the filtration steps and the filling step are performed under aseptic conditions in order to provide a sterile container comprising a sterile composition.

The invention also provides a container comprising a composition comprising fulvestrant, a pharmaceutically acceptable alcohol, polysorbate 80, an antioxidant, and castor oil. In certain embodiments, the container is a vial, an ampoule, a cartridge, or a syringe. In some embodiments, the container, the composition, or both the container and the composition are sterile.

In certain embodiments, the invention provides a pre-filled syringe containing a composition of the invention described herein. In certain embodiments, a syringe according to the invention is a component of an autoinjector. Preferably, the container is sealed by way of a closure, such as a stopper, plunger, and/or tip-cap. The container and closure can be made of glass, plastic, and/or rubber.

It has been surprisingly discovered that a composition comprising fulvestrant, a pharmaceutically acceptable alcohol, polysorbate 80, an antioxidant, and castor oil may have increased stability over a composition comprising fulvestrant, a pharmaceutically acceptable alcohol, a non-aqueous ester solvent, and castor oil, such as the FASLODEX™ (fulvestrant) injection product. The term "stability" as used herein with respect to a composition is meant to encompass any characteristic of a composition which may be affected by storage conditions including, without limitation, total impurities, fulvestrant degradation products, specific optical rotation, optical purity, water content, appearance, viscosity, sterility, and color and clarity. Methods for determining the stability of a composition of the invention with respect to a given parameter are well-known to those of skill in the art. For example, fulvestrant degradation products and total impurities can be assessed by high-performance liquid chromatography (HPLC) or thin layer chromatography (TLC).

In some embodiments, when a composition of the invention is stored at 2°-8° C., 25° C., or 40° C. for a period of 3 months, the amount of total impurities present in the composition is not more than 1%. Any suitable method can be used to determine the amount of total impurities present in the composition. Preferably, the amount of total impurities is calculated as the sum of the area under the peak of each impurity as a percentage of the total area under all peaks observed in an HPLC chromatogram. In other embodiments, when a composition of the invention is stored at 2°-8° C., 25° C., or 40° C. for a period of 3 months, the amount of total impurities present in the composition is not more than 0.9%, e.g., not more than 0.8%, not more than 0.7%, not more than 0.6%, not more than 0.5%, not more than 0.4%, not more than 0.3%, not more than 0.2%, or not more than 0.1%. In yet other embodiments, when a composition of the invention is stored at 2°-8° C., 25° C., or 40° C. for a period of 3 months, the amount of total impurities present in the composition is 0.1%-1%, 0.1%-0.8%, 0.3%-0.7%, 0.4%-0.9%, 0.1%-0.5%, or 0.2%-1%.

In certain embodiments, when a composition of the invention is stored at room temperature for a period of 12 months, the amount of total impurities present in the composition is not more than 2.0%. In other embodiments, when a composition of the invention is stored at room temperature for a period of 12 months, the amount of total impurities present in the composition is not more than 1.8%, e.g., not more than 1.6%, not more than 1.5%, not more than 1.4%, not more than 1.2%, not more than 1.0%, not more than 0.8%, not more than 0.7%, or not more than 0.6%. In yet other embodiments, when a composition of the invention is stored at room temperature for a period of 12 months, the amount of total impurities present in the composition is 0.6%-2.0%, 0.7%-1.6%, 0.8%-1.8%, 1.0%-1.5%, 0.8%-1.2%, or 0.6%-1.4%.

Fulvestrant sulfone is an oxidative degradation product of fulvestrant. In some embodiments, when a composition of the invention is stored at 2°-8° C., 25° C., or 40° C. for a period of 3 months, the amount of fulvestrant sulfone present in the composition is not more than 0.5%. Any suitable method can be used to determine the amount of fulvestrant sulfone present in the composition. Preferably, the amount of fulvestrant sulfone is calculated as the area under the fulvestrant sulfone peak as a percentage of the total area under all peaks observed in an HPLC chromatogram. In other embodiments, when a composition of the invention is stored at 2°-8° C., 25° C., or 40° C. for a period of 3 months, the amount of fulvestrant sulfone present in the composition is not more than 0.45%, e.g., not more than 0.4%, not more than 0.35%, not more than 0.3%, not more than 0.25%, not more than 0.2%, not more than 0.15%, not more than 0.1%, not more than 0.09%, not more than 0.07%, or not more than 0.05%. In yet other embodiments, when a composition of the invention is stored at 2°-8° C., 25° C., or 40° C. for a period of 3 months, the amount of fulvestrant sulfone present in the composition is 0.1%-1%, 0.1%-0.8%, 0.3%-0.7%, 0.4%-0.9%, 0.1%-0.5%, or 0.2%-1%.

In some embodiments, when a composition of the invention is stored at room temperature for a period of 12 months, the amount of fulvestrant sulfone present in the composition is not more than 1.0%. In other embodiments, when a composition of the invention is stored at room temperature for a period of 12 months, the amount of fulvestrant sulfone present in the composition is not more than 0.9%, e.g., not more than 0.8%, not more than 0.75%, not more than 0.7%, not more than 0.6%, not more than 0.55%, not more than 0.5%, not more than 0.4%, not more than 0.3%, or not more than 0.25%. In yet other embodiments, when a composition of the invention is stored at room temperature for a period of 12 months, the amount of fulvestrant sulfone present in the composition is 0.25%-1.0%, 0.25%-0.75%, 0.4%-0.8%, 0.3%-0.6%, 0.5%-1.0%, or 0.5%-0.9%.

The invention also provides a method of stabilizing a fulvestrant composition by forming a mixture comprising fulvestrant, a pharmaceutically acceptable alcohol, polysorbate 80, an antioxidant, and castor oil, thereby stabilizing the composition. The identity and amounts of fulvestrant, a pharmaceutically acceptable alcohol, polysorbate 80, an antioxidant, and castor oil present in the mixture can be the same as the identity and amounts of these components described herein with respect to a composition of the invention. Preferably, the mixture, and the composition thus formed, is substantially free, or completely free, of a non-aqueous ester solvent. The composition formed by the method of stabilizing a fulvestrant composition can have the same stability characteristics as the stability characteristics described herein with respect to a composition of the invention, particularly with regard to total impurities and fulvestrant sulfone.

The composition according to the invention is suitable for administration to a subject to treat or prevent a disease or condition. Preferably, the disease or condition is a disease or condition of the breast or of the female reproductive tract. The disease or condition can be benign, or the disease or condition can be malignant.

In some embodiments, the invention provides a method of treating hormone receptor positive metastatic breast cancer in a subject in need thereof. The method comprises administering a therapeutically effective amount of a composition of the invention to the subject, thereby treating the hormone receptor positive metastatic breast cancer in the subject. Preferably, the composition is administered to the subject by intramuscular injection. The therapeutically effective amount of a composition of the invention can be administered in a single injection, or divided into two or more injections.

The therapeutically effective amount of a composition of the invention can be determined empirically by one of ordinary skill in the art based upon, for example, the concentration of fulvestrant in the composition, the identity and severity of the disease or condition to be treated, and subject-specific considerations such as body weight or age. In some embodiments, the volume of the composition administered per injection is 5 mL or less, e.g., 4.5 mL or less, 4 mL or less, 3.5 mL or less, 3 mL or less, 2.5 mL or less, or 2 mL or less. In other embodiments, the volume of the composition administered per injection is 1 mL or more, e.g., 1.5 mL or more, 2 mL or more, 2.5 mL or more, 3 mL or more, 3.5 mL or more, or 4 mL or more. In yet other embodiments, the volume of the composition administered per injection is in a range bounded by any of the foregoing values. For example, the volume of the composition administered per injection can be 1.5 mL-3 mL, 2 mL-4 mL, 2.5 mL-4.5 mL, 3 mL-5 mL, 3.5 mL-4.5 mL, or 4 mL-4.5 mL. In certain embodiments, the volume of the composition administered per injection is about 5 mL.

A composition of the invention can be administered as a monotherapy, or a composition of the invention can be a component of a combination therapy comprising the administration of fulvestrant and one or more additional drugs. If a component of a combination therapy, a composition of the invention can be administered prior to, substantially concurrent with, or after the administration of the one or more additional drugs.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth herein are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The following examples are intended to illustrate the invention in a non-limiting manner.

EXAMPLE 1

This example demonstrates the effect of polysorbate 80 on the solubility of fulvestrant in an oil based liquid formulation.

U.S. Pat. No. 6,774,122 discloses that the solubility of fulvestrant in castor oil is 20 mg/mL, and that the solubility of fulvestrant in a castor oil vehicle containing 10% ethanol, 10% benzyl alcohol, and 15% benzyl benzoate is 65 mg/mL. To determine the effect of other compounds on the solubility of fulvestrant in a castor oil vehicle containing 10% ethanol and 10% benzyl alcohol, several liquid formulations were prepared by mixing using standard techniques, as summarized in Table 1. Fulvestrant solubility in each formulation was determined by an HPLC assay.

TABLE 1

| Component | % w/v | | | | | | | |
|---|---|---|---|---|---|---|---|---|
| Ethanol | 10 | 10 | 10 | 10 | 10 | 10 | 10 | 10 |
| Benzyl alcohol | 10 | 10 | 10 | 10 | 10 | 10 | 10 | 10 |
| Ethyl oleate | 15 | — | — | — | — | — | — | — |
| Isopropyl myristate | — | 15 | — | — | — | — | — | — |
| Isopropyl palmitate | — | — | 15 | — | — | — | — | — |
| Polysorbate 80 | — | — | — | 0.2 | 0.16 | 0.1 | 0.09 | 0.05 |
| Castor oil | q.s | q.s | q.s | q.s | q.s | q.s | q.s | q.s |
| Solubility (mg/ml) | 66.8 | 63.9 | 67.6 | 95.0 | 90.0 | 82.5 | 82.1 | 76.5 |

The solubility of fulvestrant in the presence of the non-aqueous ester solvent ethyl oleate, isopropyl myristate, or isopropyl palmitate was similar to the solubility of fulvestrant in the presence of the non-aqueous solvent, benzyl benzoate, as reported in U.S. Pat. No. 6,774,122.

Remarkably, the presence of polysorbate 80 greatly increased the solubility of fulvestrant in a castor oil based formulation, even in the absence of any non-aqueous ester solvent.

The results of this example demonstrate that polysorbate 80 enhances the solubility of fulvestrant in a castor oil based formulation to a greater extent than non-aqueous ester solvents, such as benzyl benzoate, ethyl oleate, isopropyl myristate, and isopropyl palmitate.

EXAMPLE 2

This example demonstrates the effect of polysorbate 80 and an antioxidant on the stability of an oil based liquid formulation containing fulvestrant.

The FASLODEX™ (fulvestrant) injection product must be stored under refrigeration at 2°-8° C. until the time of use. To determine the effect of polysorbate 80 and an antioxidant on the stability an oil based liquid formulation containing fulvestrant, a reference formulation representing the FASLODEX™ (fulvestrant) injection product ("RLD") and several formulations according to the invention were prepared by mixing using standard techniques, as summarized in Table 2.

TABLE 2

| Formulation | Ethanol | Benzyl alcohol | Benzyl benzoate | Polysorbate 80 (% w/v) | α-tocopherol | Fulvestrant | Castor oil |
|---|---|---|---|---|---|---|---|
| RLD | 10 | 10 | 15 | — | — | 5.0 | q.s. |
| A | 10 | 10 | — | 0.12 | 0.06 | 7.5 | q.s. |
| B | 15 | 10 | — | 0.12 | 0.06 | 10.0 | q.s. |
| C | 10 | 10 | — | 0.12 | 0.06 | 5.0 | q.s. |
| D | 17 | 10 | — | 0.12 | 0.06 | 5.0 | q.s. |

Samples of the RLD and each of Formulations A-D were stored for 3 months at 25° C. At the end of the storage period, the amounts of sulfone impurity and total impurities were measured using an HPLC assay. The results of the storage stability testing are summarized in Table 3.

TABLE 3

| Formulation | Sulfone impurity (% w/w) | Total impurities (% w/w) |
|---|---|---|
| RLD | 0.30 | 1.25 |
| A | 0.50 | 0.64 |
| B | 0.32 | 0.60 |
| C | 0.45 | 0.78 |
| D | 0.21 | 0.35 |

The amount of sulfone impurity following storage for 3 months at 25° C. was approximately the same for each of the RLD and Formulations A-D. However, the amount of total impurities was greatly reduced in each of Formulations A-D as compared with the RLD.

To further examine the effect of an antioxidant on stability, several formulations containing 5% fulvestrant, 10% ethanol, 10% benzyl alcohol, 0.06% α-tocopherol and 0.12% polysorbate 80 in castor oil were prepared and supplemented with 0%, 2%, 4%, 8%, or 12% α-tocopherol. Samples of each formulation were stored for 3 months at 2-8° C., 25° C., or 40° C. At the end of the storage period, the amounts of sulfone impurity and total impurities were measured using an HPLC assay. The results of the storage stability testing are summarized in Table 4.

TABLE 4

| Supplemental α-tocopherol | Sulfone impurity (% w/w) | | | Total impurities (% w/w) | | |
|---|---|---|---|---|---|---|
| (w/v) | 2-8° C. | 25° C. | 40° C. | 2-8° C. | 25° C. | 40° C. |
| 0.0 | 0.09 | 0.17 | 0.29 | 0.4 | 0.5 | 0.7 |
| 2.0 | 0.13 | 0.16 | 0.37 | 0.4 | 0.5 | 0.7 |
| 4.0 | 0.10 | 0.13 | 0.16 | 0.5 | 0.4 | 0.5 |
| 8.0 | 0.13 | 0.16 | 0.19 | 0.7 | 0.6 | 0.6 |
| 12.0 | 0.10 | 0.19 | 0.25 | 0.8 | 0.8 | 0.7 |

The amounts of sulfone impurity and total impurities were similar following storage for 3 months at 2-8° C., 25° C., or 40° C. irrespective of the amount of α-tocopherol added to the base formulation which contained 0.06% α-tocopherol.

The results of this example demonstrate that the combination of polysorbate 80 and an antioxidant increases the stability of fulvestrant in oil based liquid formulations.

EXAMPLE 3

This example demonstrates the pharmacokinetics of fulvestrant following administration of an oil based liquid formulation containing benzyl benzoate or a combination of polysorbate 80 and an antioxidant.

A dose of 33.33 mg/kg of the commercial FASLODEX™ (fulvestrant) injection product or one of Formulations A-D as described in Example 2 was delivered by injection to the buttocks of female rabbits (n=6 per group). The dose volume was divided equally on two sites of injection per rabbit. Blood samples were collected prior to dosing, and at 2, 4, 6, 8, 12, 16, 24, 48, 72, 120, 168, 336, 504, and 672 hours after dosing. The concentration of fulvestrant in the plasma was determined using an HPLC assay.

The time course of fulvestrant plasma concentration was similar in rabbits dosed with the FASLODEX™ product or any one of Formulations A-D (FIG. 1). The mean $T_{max}$ and $C_{max}$, and the mean AUC relative to the FASLODEX™ product observed in this study are summarized in Table 5.

TABLE 5

| Treatment | $T_{max}$ (hr) | $C_{max}$ (ng/mL) | Relative $AUC_{0-t}$ (ng * hr/mL) | Relative $AUC_{inf}$ (ng * hr/mL) |
|---|---|---|---|---|
| FASLODEX ™ | 84 | 21.7 | 100 | 100 |
| A | 96 | 17.6 | 92.3 | 111 |
| B | 60 | 17.8 | 81.2 | 92.1 |
| C | 120 | 18.7 | 95.9 | 97.2 |
| D | 120 | 20.0 | 93.9 | 102 |

A one-way ANOVA of log-transformed data of the calculated $C_{max}$, $AUC_{0-t}$, and $AUC_{inf}$ values yielded p-values of 0.1938, 0.1431, and 0.1071, respectively. Thus, there was no significant difference in the $C_{max}$, $AUC_{0-t}$, and $AUC_{inf}$ achieved following administration to rabbits of the FASLODEX™ product as compared to any one of Formulations A-D.

The results of this example demonstrate that oil based liquid formulations containing fulvestrant, polysorbate 80, and an antioxidant provide similar pharmacokinetics as an oil based liquid formulation containing fulvestrant and the non-aqueous ester solvent, benzyl benzoate.

EXAMPLE 4

This example demonstrates a method for making a composition comprising fulvestrant, a pharmaceutically acceptable alcohol, polysorbate 80, an antioxidant, and castor oil.

An exemplary composition according to the invention is described in Table 6.

TABLE 6

| Component | Amount |
|---|---|
| Fulvestrant | 50 mg/mL |
| Ethyl alcohol, 190 proof, NF | 10% |
| Benzyl alcohol, USP | 10% |
| Polysorbate 80 | 0.12% |
| α-tocopherol | 0.06% |
| Castor oil (super refined) | q.s. |

The composition is prepared according to the following general procedure. Benzyl alcohol is added into a stainless steel tank held at room temperature. Ethyl alcohol is added into the tank, and the composition is mixed for not less than 5 minutes. Fulvestrant is added into the tank, and the composition is mixed for not less than 30 minutes until the fulvestrant is dissolved. Polysorbate 80 and α-tocopherol are added into the tank, and the composition is mixed for not less than 5 minutes. Super refined castor oil is added to the tank to approximately 70% of the final volume. The tank is pressurized with nitrogen, and the composition is mixed for not less than 30 minutes. Super refined castor oil is added to the tank until the final volume is obtained. The tank is pressurized with nitrogen, and the composition is mixed for not less than 60 minutes, at which point the composition should be clear to slightly hazy. The composition is filtered through a pre-filter having a pore diameter of 0.45 μm into a suitable vessel.

The composition is then filtered through a final filter having a pore diameter of 0.2 μm into a pressure tank fitted with a filling needle under aseptic conditions. The composition is dispensed into a suitable container, and the filled container is sealed.

This example provides a suitable method to prepare a composition according to the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A composition, comprising:
   fulvestrant,
   a pharmaceutically acceptable alcohol,
   polysorbate 80,
   an antioxidant, and
   castor oil,
   wherein the composition is substantially free of a non-aqueous ester solvent.

2. The composition of claim 1, wherein the composition is completely free of a non-aqueous ester solvent.

3. The composition of claim 1, wherein the antioxidant is a vitamin E compound.

4. The composition of claim 3, wherein the vitamin E compound is α-tocopherol.

5. The composition of claim 1, wherein the pharmaceutically acceptable alcohol comprises a mixture of ethanol and benzyl alcohol.

6. The composition of claim 5, wherein the ethanol and benzyl alcohol are present in approximately equivalent w/v amounts.

7. The composition of claim 6, comprising 10% w/v ethanol and 10% w/v benzyl alcohol.

8. The composition of claim 1, wherein the castor oil is characterized by a carbonyl value of 0.5 micromole/gram or less, a peroxide value of 5.0 meq $O_2$/kg or less, an iodine value of 85 g iodine/100 g castor oil or less, and/or a Gardner 1933 value of 1.5 or less.

9. The composition of claim 1, wherein following storage of the composition at 25° C. for a period of 3 months, the amount of total impurities present in the composition is not more than 1%.

10. The composition of claim 1, wherein following storage of the composition at 25° C. for a period of 3 months, the amount of fulvestrant sulfone present in the composition is not more than 0.5%.

11. The composition of claim 1, comprising 5-10% w/v fulvestrant, 10-30% w/v pharmaceutically acceptable alcohol, and 0.05-0.2% w/v polysorbate 80.

12. A syringe comprising 2.5 mL-5 mL of the composition of claim 1.

13. A vial comprising 2.5 mL-5 mL of the composition of claim 1.

14. A composition, comprising:
   5% w/v fulvestrant,
   10% ethanol,
   10% benzyl alcohol,
   0.12% w/v polysorbate 80,
   0.06% a-tocopherol, and
   castor oil,
   wherein the composition is substantially free of a non-aqueous ester solvent.

15. A method of stabilizing a fulvestrant composition, comprising forming a mixture comprising:
   5-10% w/v fulvestrant,
   10-30% w/v pharmaceutically acceptable alcohol,
   0.05-0.2% w/v polysorbate 80,
   an antioxidant, and
   castor oil,
   thereby stabilizing a fulvestrant composition,
   wherein the mixture is substantially free of a non-aqueous ester solvent.

16. The method of claim 15, wherein following storage of the composition at 25° C. for a period of 3 months, the amount of total impurities present in the composition is not more than 1%.

17. A method of treating hormone receptor positive metastatic breast cancer in a subject in need thereof, comprising administering a therapeutically effective amount of the composition of claim 1 to the subject, thereby treating the hormone receptor positive metastatic breast cancer in the subject.

* * * * *